(12) United States Patent
Kuo et al.

(10) Patent No.: US 8,273,917 B2
(45) Date of Patent: Sep. 25, 2012

(54) METHOD FOR PREPARING CHIRAL BACLOFEN

(75) Inventors: Jen-Huang Kuo, Hsinchu (TW); Wei-chyun Wong, Hsinchu (TW)

(73) Assignee: Sci Pharmtech, Inc. (TW)

( * ) Notice: Subject to any disclaimer, the term of this patent is extended or adjusted under 35 U.S.C. 154(b) by 184 days.

(21) Appl. No.: 12/844,574

(22) Filed: Jul. 27, 2010

(65) Prior Publication Data
US 2012/0029230 A1    Feb. 2, 2012

(51) Int. Cl.
*C07C 229/08*    (2006.01)

(52) U.S. Cl. ...................................................... 562/442
(58) Field of Classification Search ................. 562/442
See application file for complete search history.

(56) References Cited

U.S. PATENT DOCUMENTS
6,051,734 A * 4/2000 Wildervanck et al. ........ 562/573
* cited by examiner

*Primary Examiner* — Rebecca Anderson
*Assistant Examiner* — Sonya Wright
(74) *Attorney, Agent, or Firm* — Berliner & Associates

(57) ABSTRACT

The present invention provides a novel method for preparing chiral Baclofen with higher yield, higher e.e. value, and lower cost via chiral Michael addition.

13 Claims, No Drawings

METHOD FOR PREPARING CHIRAL BACLOFEN

BACKGROUND OF THE INVENTION

1. Field of the Invention

The present invention relates to a novel method for preparing chiral Baclofen, (R)-(+)-β-(Aminomethyl)-4-chlorobenzenepropanoic acid.

2. Description of Related Art

Baclofen is an analog of gamma-aminobutyric acid (GABA) that selectively activates $GABA_B$ receptor and is used for treatment of spasticity. It has one chiral center and currently available medicines are of racemic type. It is known that the R-form bears the biological activity. There are many publications about the preparation of R-Baclofen. For example, U.S. Pat. No. 6,051,734 discloses the following scheme:

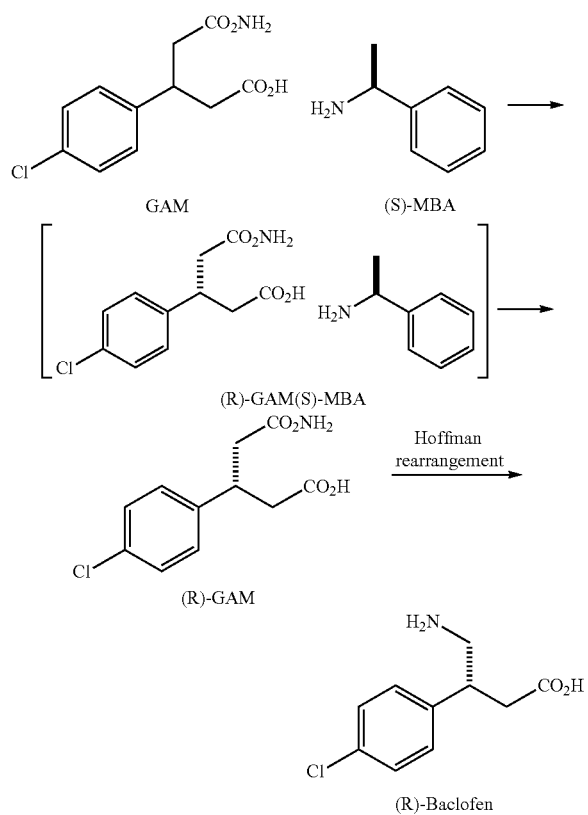

In this example, racemic 3-(p-chlorophenyl)glutaramide (GAM) is resolved with (S)-(−)-α-methylbenzylamine ((S)-MBA) to form salt of (R)-GAM(S)-MBA which is further converted to (R)-GAM. (R)-GAM is then transformed to (R)-Baclofen via Hoffman rearrangement. The yield from GAM to (R)-GAM is 15.9% (referring to EXAMPLE 2 of U.S. Pat. No. 6,051,734) and yield of Hoffman rearrange is 57.6% (referring to EXAMPLE 4 of U.S. Pat. No. 6,051,734). Overall yield of this process is only 9.2% that rendered this process commercially less competitive.

Accordingly, there is a demand for a simple and more efficient process for preparing (R)-Baclofen with higher yield and lower cost.

SUMMARY OF THE INVENTION

In light of the above-mentioned drawbacks of the prior art, the present invention provides a novel method for preparing (R)-Baclofen of formula I.

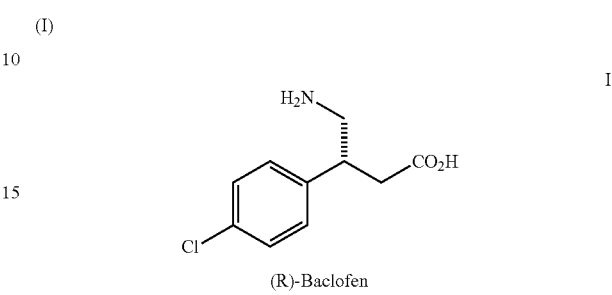

The method of preparing (R)-Baclofen of formula I of the present invention includes steps of: (i) reacting p-chlorocinamic acid with a chiral auxiliary compound of formula II to form a compound of formula III; (ii) performing Michael addition of nitromethane to the compound of formula III to give a compound of formula IV in good diastereomeric selection; (iii) performing hydrolysis of the compound of formula IV to obtain a compound of formula V and recover the chiral auxiliary compound of formula II; and (iv) reducing nitro group of the compound of formula V to yield (R)-Baclofen of formula I.

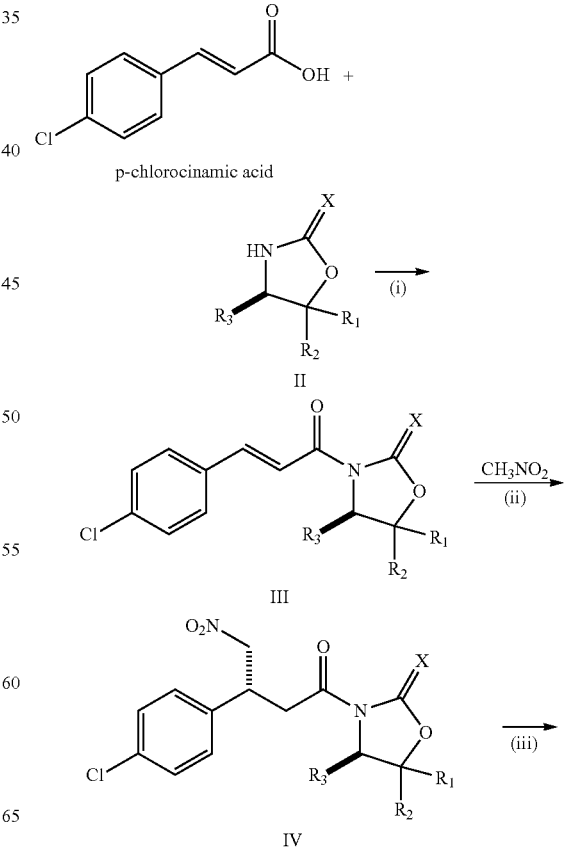

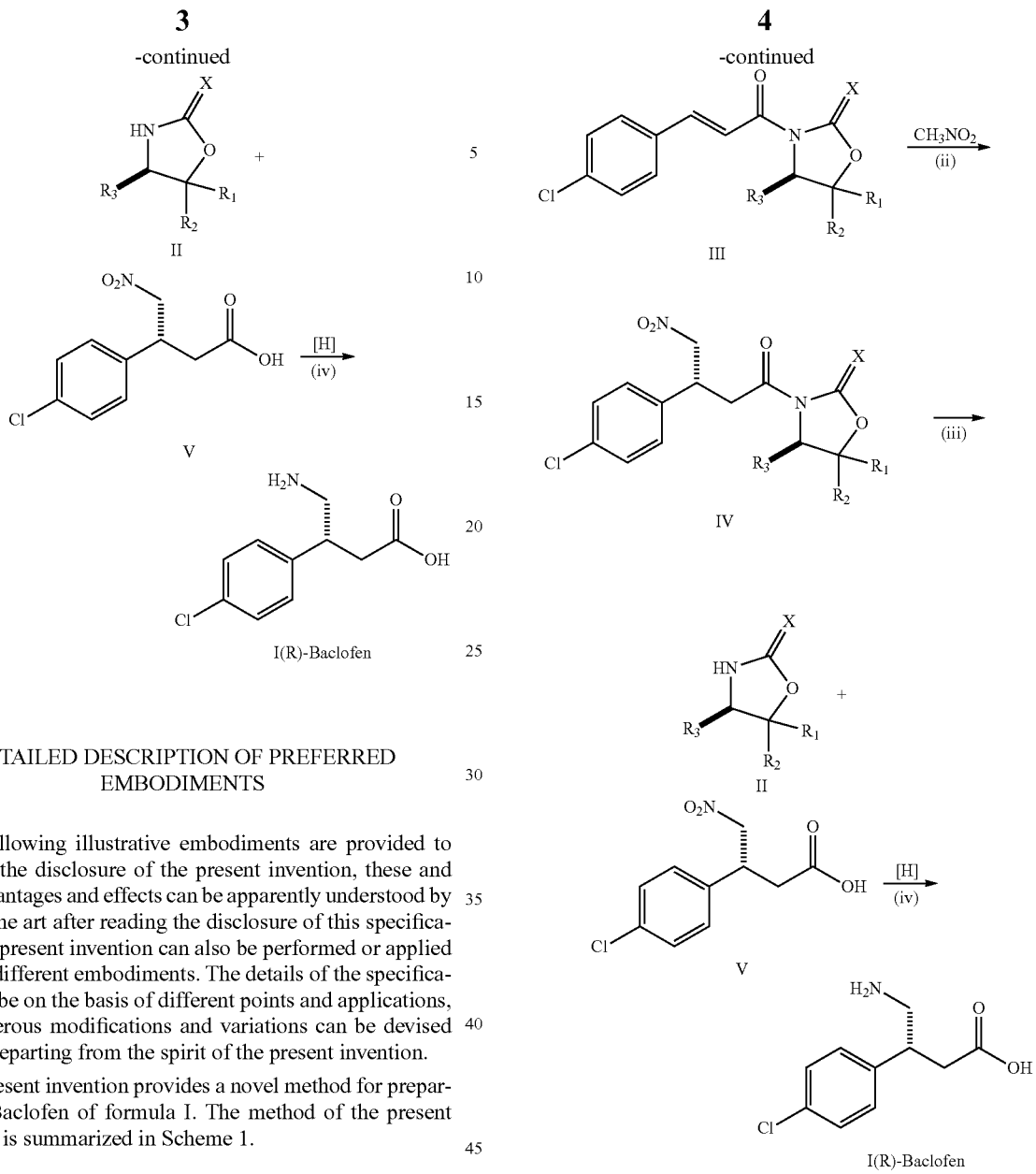

DETAILED DESCRIPTION OF PREFERRED EMBODIMENTS

The following illustrative embodiments are provided to illustrate the disclosure of the present invention, these and other advantages and effects can be apparently understood by those in the art after reading the disclosure of this specification. The present invention can also be performed or applied by other different embodiments. The details of the specification may be on the basis of different points and applications, and numerous modifications and variations can be devised without departing from the spirit of the present invention.

The present invention provides a novel method for preparing (R)-Baclofen of formula I. The method of the present invention is summarized in Scheme 1.

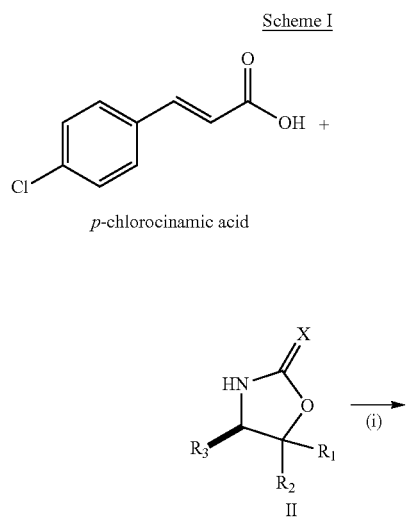

In scheme I, $R_1$ and $R_2$ are independently a hydrogen atom, an alkyl group having 1 to 8 carbon atoms or an aryl group having 6 to 10 carbon atoms; $R_3$ is an alkyl group having 1 to 8 carbon atoms or an aryl group having 6 to 10 carbon atoms; and X is a hetero atom such as N, O and S.

In more details, the method of the present invention includes steps of reacting p-chlorocinamic acid with a chiral auxiliary compound of formula II to form a compound of formula III; performing Michael addition of nitromethane to the compound of formula III to give a compound of formula IV in good diastereomeric selection; performing hydrolysis of the compound of formula IV to obtain a compound of formula V and recover the chiral auxiliary compound of formula II; and reduing nitro group of the compound of formula V to yield (R)-Baclofen of formula I.

In comparison with the conventional process, (R)-Baclofen of formula I can be obtained optically pure with higher yield and lower cost in the present invention.

EMBODIMENTS

Step 1: Preparation of a Compound of the Following Formula III

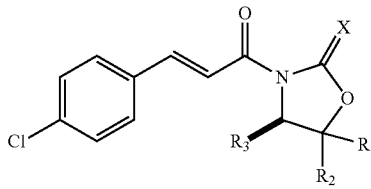

EXAMPLE 1

$R_1=R_2=H$, $R_3=Ph$, $X=O$ 18.3 g of p-chlorocinamic acid, 17.0 g of $SOCl_2$, 100 g of anhydrous toluene and two drops of DMF were charged into a flask. After stirred at reflux temperature for 3.5 hours, the reaction mixture was cooled down to room temperature. Toluene was removed under reduced pressure to give a residue and then charged in with 80 g of $CH_2Cl_2$. 15.2 g of (S)-4-phenyl-2-oxazolidinone (formula II), 11.1 g of $Et_3N$ and 200 g of $CH_2Cl_2$ were charged in another flask. The resulting suspension was stirred for 20 minutes, kept in an ice-bath and then charged in the above acid chloride/$CH_2Cl_2$ solution dropwisely. The mixture was warmed up slowly to room temperature and stirred for another 20 hours. The salt was filtered and the organic solvent was removed under reduced pressure. The residue was then re-crystallized with isopropyl alcohol to give 30.7 g of the compound of the formula III (93.9% yield). $^1$H NMR (300 MHz, $CDCl_3$): δ (ppm)=7.91 (d, J=18.0 Hz, 1H, ArCH=CH), 7.72 (d, J=15.0 Hz, 1H, ArCH=CH), 7.53-7.34 (m, 9H, ArH), 5.56 (dd, J=3.0 Hz and 9.0 Hz, 1H, CHPh), 4.75 (dd, J=9.0 Hz and 9.0 Hz, 1H, PhCHCHH), 4.34 (dd, J=3.0 Hz and 7.5 Hz, 1H, PhCHCHH); $^{13}$C NMR (75 MHz, $CDCl_3$): δ (ppm)=164.6, 153.9, 145.2, 139.1, 136.7, 133.1, 129.9, 129.4, 129.3, 128.9, 126.1, 117.5, 70.1, 58.0.

EXAMPLE 2

The reaction procedure was the same as that of EXAMPLE 1 except for $R_1=R_2=Ph$, $R_3=iPr$ and $X=O$.
$^1$H NMR (300 MHz, $CDCl_3$): δ (ppm)=7.84 (d, J=15.0 Hz, 1H, ArCH=CH), 7.75 (d, J=15.0 Hz, 1H, ArCH=CH), 7.52-7.24 (m, 14H, ArH), 5.54 (d, J=3.0 Hz, 1H, CHiPr), 2.03 (m, 1H, $CH_3CHCH_3$), 0.93 (d, J=6.0 Hz, 3H, $CH_3$), 0.81 (d, J=9.0 Hz, 3H, $CH_3$); $^{13}$C NMR (75 MHz, $CDCl_3$): δ (ppm)=165.0, 153.2, 145.1, 142.4, 138.3, 136.6, 133.1, 129.9, 129.2, 129.1, 128.7, 128.5, 128.1, 126.1, 125.8, 117.4, 89.6, 64.6, 30.3, 21.9, 16.5.

EXAMPLE 3

The reaction procedure was the same as that of EXAMPLE 1 except for $R_1=R_2=Ph$, $R_3=iPr$ and $X=S$.
$^1$H NMR (300 MHz, $CDCl_3$): δ (ppm)=8.39 (d, J=15.0 Hz, 1H, ArCH=CH), 7.65 (d, J=15.0 Hz, 1H, ArCH=CH), 7.52-7.19 (m, 14H, ArH), 5.69 (d, J=3.0 Hz, 1H, CHiPr), 2.13-2.03 (m, 1H, $CH_3CHCH_3$), 0.91 (d, J=6.0 Hz, 3H, $CH_3$), 0.83 (d, J=6.0 Hz, 3H, $CH_3$)

Step 2: Preparation of a Compound of the Following Formula IV

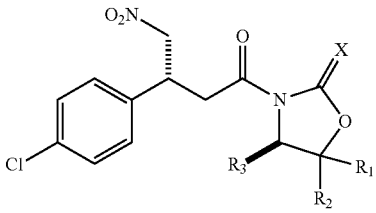

EXAMPLE 4

$R_1=R_2=H$, $R_3=Ph$, $X=O$ 1.0 g of nitromathane, 0.045 g of tetramethyl guanidine and 10 g of $CH_2Cl_2$ were charged into a flask. The reaction mixture was cooled down to 0 to 4° C. A solution containing 0.25 g of the compound of formula III and 5 g of $CH_2Cl_2$ was added over a period of 10 minutes. The resulting mixture was stirred for 24 hours at 0 to 4° C. and then warmed up to room temperature. The reaction was quenched with 5 g of 1N HCl aqueous solution. After separation, $CH_2Cl_2$ and nitromethane were removed from the organic layer under reduced pressure. The crude product was purified by column chromatography to obtain 0.24 g of the compound of formula IV as a diastereomeric mixture (82.5% yield). Diastereomeric ratio between (4S, 3'S) and (4S, 3'R) was determined to be 62/38 by HPLC. $^1$H NMR (300 MHz, $CDCl_3$): δ (ppm)=7.32-7.03 (m, 9H, ArH), 5.39 (dd, J=3.0 Hz and 7.5 Hz, 1H, CHPh), 4.69 (dd, J=9.0 Hz and 9.0 Hz, 1H, PhCHCHH), 4.65-4.55 (m, 2H, $NO_2CH_2$), 4.25 (dd, J=3.0 Hz and 9.0 Hz, 1H, PhCHCHH), 4.04-3.99 (m, 1H, ArCH), 3.65 (dd, J=6.0 Hz and 16.5 Hz, 1H, CHHCON), 3.21 (dd, J=9.0 Hz and 16.5 Hz, 1H, CHHCON)

EXAMPLE 5

$R_1=R_2=Ph$, $R_3=iPr$, $X=O$ 103 g of nitromathane, 3.2 g of tetramethyl guanidine and 50 g of DMF were charged into a flask. The reaction mixture was cooled down to −50° C. A solution containing 25 g of the compound of formula III and 500 g of DMF was added over a period of 30 minutes. The resulting mixture was stirred for 12 hours at −50° C. and then warmed up to room temperature. The reaction was quenched with 50 g of 1N HCl aqueous solution. DMF and nitromethane were removed under reducing pressure. The residue was charged with 550 g of $H_2O$ and crude product was obtained. Diastereomeric ratio between (4S, 3'S) and (4S, 3'R) was determined to be 93/7 by HPLC. After filtration, the crude product was re-crystallized with ethyl acetate to give 22.1 g of the compound of formula IV (78% yield, de=99%). $^1$H NMR (300 MHz, $CDCl_3$): δ (ppm)= 7.34-7.20 (m, 10H, ArH), 7.16 (d, J=9.0 Hz, 2H, ArH), 7.04 (d, J=9.0, 2H, ArH), 5.26 (d, J=3.0 Hz, 1H, CHiPr), 4.62-4.49 (m, 2H, $NO_2CH_2$), 4.05 (p, J=6.0 Hz, 1H, ArCH); 3.44 (dd, J=6.0 Hz and 15.0 Hz, 1H, CHHCON), 3.18 (dd, J=6.0 Hz and 18.0 Hz, 1H, CHHCON), 1.97-1.91 (m, 1H, $CH_3CHCH_3$), 0.82 (d, J=9.0 Hz, 3H, $CH_3$), 0.72 (d, J=9 Hz, 3H, $CH_3$); $^{13}$C NMR (75 MHz, $CDCl_3$): δ (ppm)=169.6, 153.1, 141.8, 137.8, 136.7, 133.7, 129.2, 129.0, 128.8, 128.7, 128.5, 128.2, 125.9, 125.4, 90.0, 79.5, 64.7, 39.1, 37.7, 29.8, 21.7, 16.5.

EXAMPLE 6

The reaction procedure was the same as that of EXAMPLE 5 except for $R_1=R_2=Ph$, $R_3=iPr$ and $X=S$.

Diastereomeric ratio between (4S,3'S) and (4S,3'R) was determined to be 71/29 by HPLC. $^1H$ NMR (300 MHz, $CDCl_3$): δ (ppm)=7.43-7.09 (m, 14H, ArH), 5.45 (d, J=3.0 Hz, 1H, CHiPr), 4.62-4.42 (m, 2H, $NO_2CH_2$), 4.01 (p, J=9.0 Hz, 1H, ArCH); 3.85 (dd, J=6.0 Hz and 18.0 Hz, 1H, CHH-CON), 3.50 (dd, J=6.0 Hz and 12.0 Hz, 1H, CHHCON), 2.04-1.92 (m, 1H, $CH_3CHCH_3$), 0.80 (d, J=9.0 Hz, 3H, $CH_3$), 0.66 (d, J=9 Hz, 3H, $CH_3$)

Step 3 and Step 4: Preparation of Compounds of the Following Formulae V and I

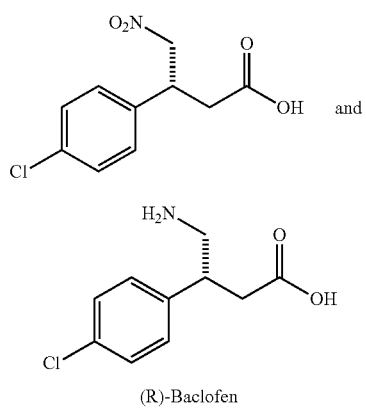

EXAMPLE 7

40 g of the compound of formula IV, 200 g of MeOH and 4 g of water were charged into a flask. The resulting suspension was added with 6.9 g of NaOH, stirred for 2 hours at room temperature and the precipitate (the compound of formula II) was filtered. The compound of formula II was isolated as a white solid (20.4 g, 92% recovery yield). The filtrate containing the compound of formula V was added with 4.0 g of Raney-Ni (50% wet) and hydrogenated (5 atm at 50° C.) for 14 hours. The catalyst was then filtered and pH of the filtrate was adjusted to 8 to precipitate out crude Baclofen. After filtration, the crude Baclofen was re-crystallized from water to obtain 10.9 g of (R)-(−)-4-amino-3-(4-chlorophenyl) butanoic acid (R-Baclofen, 65% chemical yield, 99.3% e.e.). $^1H$ NMR (300 MHz, D2O): δ (ppm)=7.32 (d, J=9.0 Hz, 2H, ArH), 7.20 (d, J=6.0 Hz, 2H, ArH), 3.22-3.05 (m, 3H, $NH_2CH_2$, ArCH), 2.50 (dd, J=6.0 Hz and 15.0 Hz, 1H, CHH-COOH), 2.39 (dd, J=6.0 and 13.5, 1H, CHHCOOH); $^{13}C$ NMR (75 MHz, D2O): δ (ppm)=179.5, 138.2, 133.1, 129.5, 129.2, 44.1, 42.2, 40.8.

The foregoing descriptions of the detailed embodiments are only illustrated to disclose the features and functions of the present invention and not restrictive of the scope of the present invention. It should be understood to those in the art that all modifications and variations according to the spirit and principle in the disclosure of the present invention should fall within the scope of the appended claims.

What is claimed is:

1. A method for preparing (R)-Baclofen of formula (I),

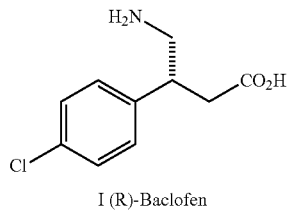

I (R)-Baclofen comprising the steps of:

reacting p-chlorocinamic acid with a chiral auxiliary compound of formula II to form a compound of formula III;

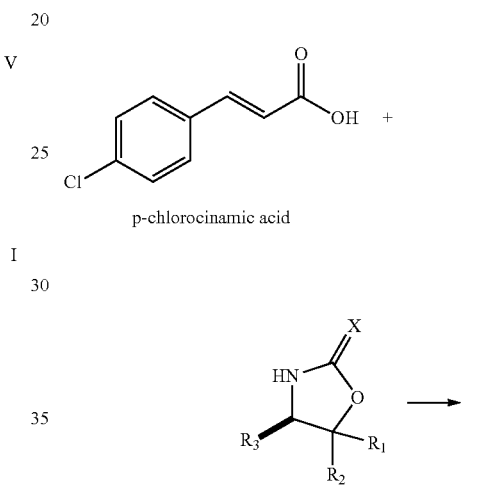

performing Michael addition of nitromethane to a compound of formula III to give a compound of formula IV via diastereomeric selection;

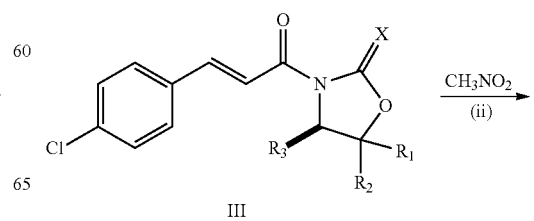

-continued

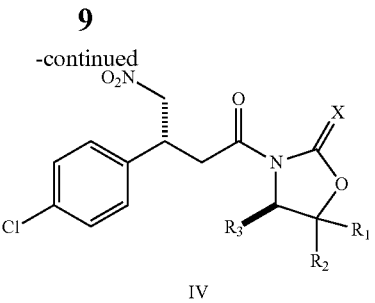

IV performing hydrolysis of the compound of formula IV to obtain a compound of formula V and recover the chiral auxiliary compound of formula II;

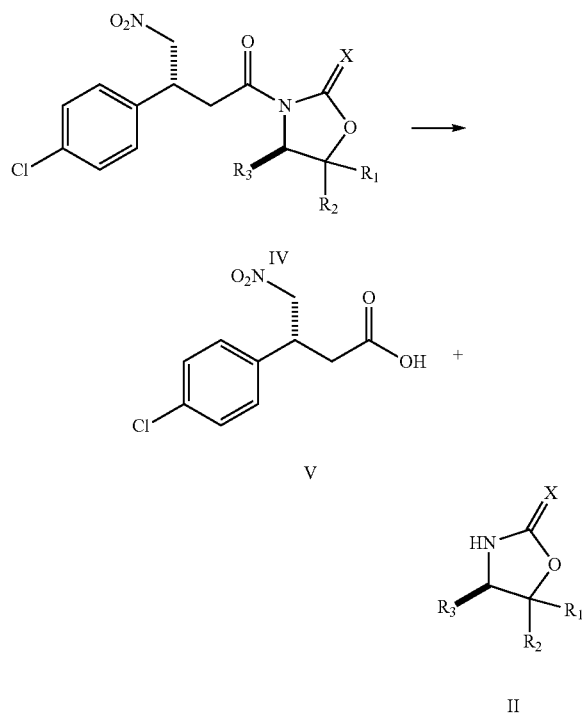

and reducing a nitro group of the compound of formula V to yield (R)-Baclofen of formula I,

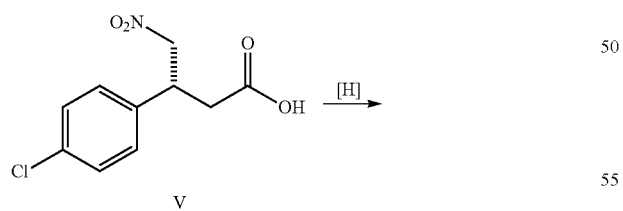

-continued

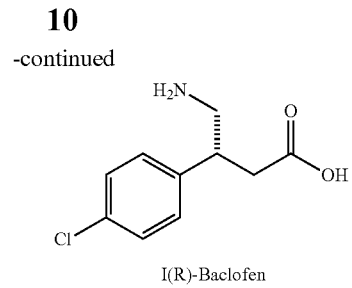

I(R)-Baclofen wherein $R_1$ and $R_2$ are independently a hydrogen atom, an alkyl group having 1 to 8 carbon atoms or an aryl group having 6 to 10 carbon atoms; $R_3$ is an alkyl group having 1 to 8 carbon atoms or an aryl group having 6 to 10 carbon atoms; and X is N, O or S.

2. The method of claim 1, wherein the step of reacting p-chlorocinamic acid with the chiral auxiliary compound of formula II is performed in $CH_2Cl_2$ solution.

3. The method of claim 1, wherein the step of reacting p-chlorocinamic acid with the chiral auxiliary compound of formula II is performed for 1 to 30 hours.

4. The method of claim 1, wherein the Michael addition is performed with addition of $CH_2Cl_2$.

5. The method of claim 1, wherein the Michael addition is performed in the presence of tetramethyl guanidine.

6. The method of claim 1, wherein the Michael addition is performed with addition of DMF.

7. The method of claim 1, wherein the Michael addition is performed for 5 to 20 hours.

8. The method of claim 1, wherein the Michael addition is performed at a temperature in a range from −60 to −30° C.

9. The method of claim 1, wherein the step of performing hydrolysis of the compound of formula IV is performed in the presence of methanol.

10. The method of claim 1, wherein the step of performing hydrolysis of the compound of formula IV is performed in the presence of NaOH.

11. The method of claim 1, wherein the step of reducing the nitro group of the compound of formula V is performed in the presence of nickel-aluminum alloy or palladium containing catalyst or other suitable hydride.

12. The method of claim 1, wherein the step of reducing the nitro group of the compound of formula V is performed at a temperature in a range from 30 to 100° C.

13. The method of claim 1, wherein the step of reducing the nitro group of the compound of formula V is performed for 1 to 25 hours.

* * * * *